(12) United States Patent
Sanchez

(10) Patent No.: US 8,864,794 B2
(45) Date of Patent: Oct. 21, 2014

(54) SURGICAL INSTRUMENT WITH A UNIVERSAL WRIST

(75) Inventor: Dan Sanchez, Santa Barbara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1731 days.

(21) Appl. No.: 11/517,813

(22) Filed: Sep. 8, 2006

(65) Prior Publication Data

US 2007/0066986 A1 Mar. 22, 2007

Related U.S. Application Data

(63) Continuation of application No. 10/460,382, filed on Jun. 11, 2003, now Pat. No. 7,121,781.

(51) Int. Cl.
| | | |
|---|---|---|
| *A61B 17/00* | (2006.01) | |
| *B25J 9/00* | (2006.01) | |
| *B25J 3/04* | (2006.01) | |
| *B25J 17/02* | (2006.01) | |
| *B25J 13/02* | (2006.01) | |
| *A61B 19/00* | (2006.01) | |

(52) U.S. Cl.
CPC .............. *A61B 19/22* (2013.01); *B25J 9/0039* (2013.01); *A61B 2019/2226* (2013.01); *B25J 3/04* (2013.01); *B25J 17/0266* (2013.01); *B25J 13/02* (2013.01); *A61B 2019/2223* (2013.01); *A61B 2019/2234* (2013.01); *A61B 19/5212* (2013.01); *A61B 19/2203* (2013.01)
USPC ........................................................ 606/205

(58) Field of Classification Search
CPC ...... B25J 15/009; B25J 15/0028; B25J 17/02; B25J 17/0283
USPC ...................... 606/1, 30, 205, 130, 206–211; 74/490.06; 414/1
See application file for complete search history.

(56) References Cited

U.S. PATENT DOCUMENTS

| | | |
|---|---|---|
| 3,628,535 A | 12/1971 | Ostrowsky et al. |
| 4,499,790 A | 2/1985 | Helms |
| 4,604,016 A | 8/1986 | Joyce |
| 4,723,460 A | 2/1988 | Rosheim |
| 4,739,241 A | 4/1988 | Vachtsevanos et al. |
| 4,805,477 A | 2/1989 | Akeel |
| 5,053,687 A | 10/1991 | Merlet |
| 5,239,883 A | 8/1993 | Rosheim |
| 5,454,827 A | 10/1995 | Aust et al. |

(Continued)

FOREIGN PATENT DOCUMENTS

WO   WO-03001986 A2   1/2003

OTHER PUBLICATIONS

Lazerevic, Zoran, Master's Thesis entitled "Feasibility of a Steward platform with Fixed Actuators as a Platform for CABG Surgery Device" Columbia University, New York, Department of Bioengineering, (1997 pp. 1-45).

(Continued)

*Primary Examiner* — Thomas McEvoy

(57) ABSTRACT

A robotically controlled endoscopic medical instrument that includes an end effector coupled to a wrist. The wrist provides two separate degrees of freedom about the same pivot point. The end effector can be moved and actuated by pins. The pins allow for a compact minimally invasive medical instrument that has a wrist with two degrees of freedom.

19 Claims, 5 Drawing Sheets

(56) References Cited

U.S. PATENT DOCUMENTS

| | | | |
|---|---|---|---|
| 5,474,571 | A | 12/1995 | Lang |
| 5,699,695 | A | 12/1997 | Canfield |
| 5,715,729 | A | 2/1998 | Toyama et al. |
| 5,740,699 | A | 4/1998 | Ballantyne et al. |
| 5,792,135 | A | 8/1998 | Madhani et al. |
| 5,797,900 | A | 8/1998 | Madhani et al. |
| 5,808,665 | A | 9/1998 | Green |
| 5,938,678 | A | 8/1999 | Zirps et al. |
| 6,001,108 | A * | 12/1999 | Wang et al. ............ 606/130 |
| 6,102,850 | A | 8/2000 | Wang et al. |
| 6,132,441 | A | 10/2000 | Grace |
| 6,196,081 | B1 | 3/2001 | Yau |
| 6,270,453 | B1 | 8/2001 | Sakai |
| 6,296,635 | B1 | 10/2001 | Smith et al. |
| 6,307,285 | B1 | 10/2001 | Delson et al. |
| 6,312,435 | B1 | 11/2001 | Wallace et al. |
| 6,330,837 | B1 | 12/2001 | Charles et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,425,177 | B1 | 7/2002 | Akeel |
| 6,685,698 | B2 | 2/2004 | Morley et al. |
| 6,699,235 | B2 | 3/2004 | Wallace et al. |
| 6,817,974 | B2 | 11/2004 | Cooper |
| 7,121,781 | B2 | 10/2006 | Sanchez |
| 2003/0018323 | A1 * | 1/2003 | Wallace et al. ............ 606/1 |
| 2003/0028217 | A1 | 2/2003 | Nakamura et al. |
| 2003/0135204 | A1 * | 7/2003 | Lee et al. ............ 606/1 |

OTHER PUBLICATIONS

Medical Robotics @UC Berkeley Robotic Telesurgical workstation . . . robotics.eecs.berkeley.edu/medical/laparobot. html—dowloaded from world wide web on 8/28/20067 pages.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

* cited by examiner

SURGICAL INSTRUMENT WITH A UNIVERSAL WRIST

CROSS REFERENCE TO RELATED APPLICATIONS

The present application is a continuation application which claims priority from U.S. patent application Ser. No. 10/460,382, filed Jun. 11, 2003, now U.S. Pat. No. 7,121,781, which is incorporated herein by reference.

BACKGROUND OF THE INVENTION

1. Field of the Invention

The present invention relates to a robotically controlled medical instrument.

2. Background Information

Historically, surgery has been performed by making large incisions in a patient to provide access to the surgical site. There has been developed endoscopic instruments that allow a surgeon to perform a procedure through small incisions in the patient. The instruments include an endoscope which has a camera that allows the surgeon to view the internal organs of the patient. Such procedures are less traumatic to the patient and have shorter recovery times than conventional surgical procedures. Endoscopic instruments have even been used to perform minimally invasive heart surgery.

Blockage of a coronary artery may deprive the heart of blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform minimally invasive surgery, including CABG procedures. The procedure is performed with instruments that are inserted through small incisions in the patient's chest. The instruments are controlled by robotic arms. Movement of the robotic arms and actuation of instrument end effectors are controlled by the surgeon through a pair of handles and a foot pedal that are coupled to an electronic controller.

It is generally desirable to maximize the degrees of freedom while minimizing the size of the instrument inserted into the patient. Multiple degrees of freedom improve the dexterity of the system. Small compact instruments minimize the size of the incision in the patient.

U.S. Pat. No. 6,296,635 issued to Smith et al. discloses a medical instrument that has a number of different degrees of freedom. The instrument is moved and actuated by a series of cables and pulleys. Cable/pulley systems are relatively bulky and not conducive to small compact packaging.

BRIEF SUMMARY OF THE INVENTION

A robotically controlled medical instrument that includes an end effector coupled to a wrist. The wrist provides the end effector with two degrees of freedom about the same pivot point.

DETAILED DESCRIPTION

Disclosed is a robotically controlled endoscopic medical instrument that includes an end effector coupled to a wrist. The wrist provides two separate degrees of freedom about the same pivot point. The end effector can be moved and actuated by pins. The pins allow for a compact minimally invasive medical instrument that has a wrist with two degrees of freedom.

Figure 1:
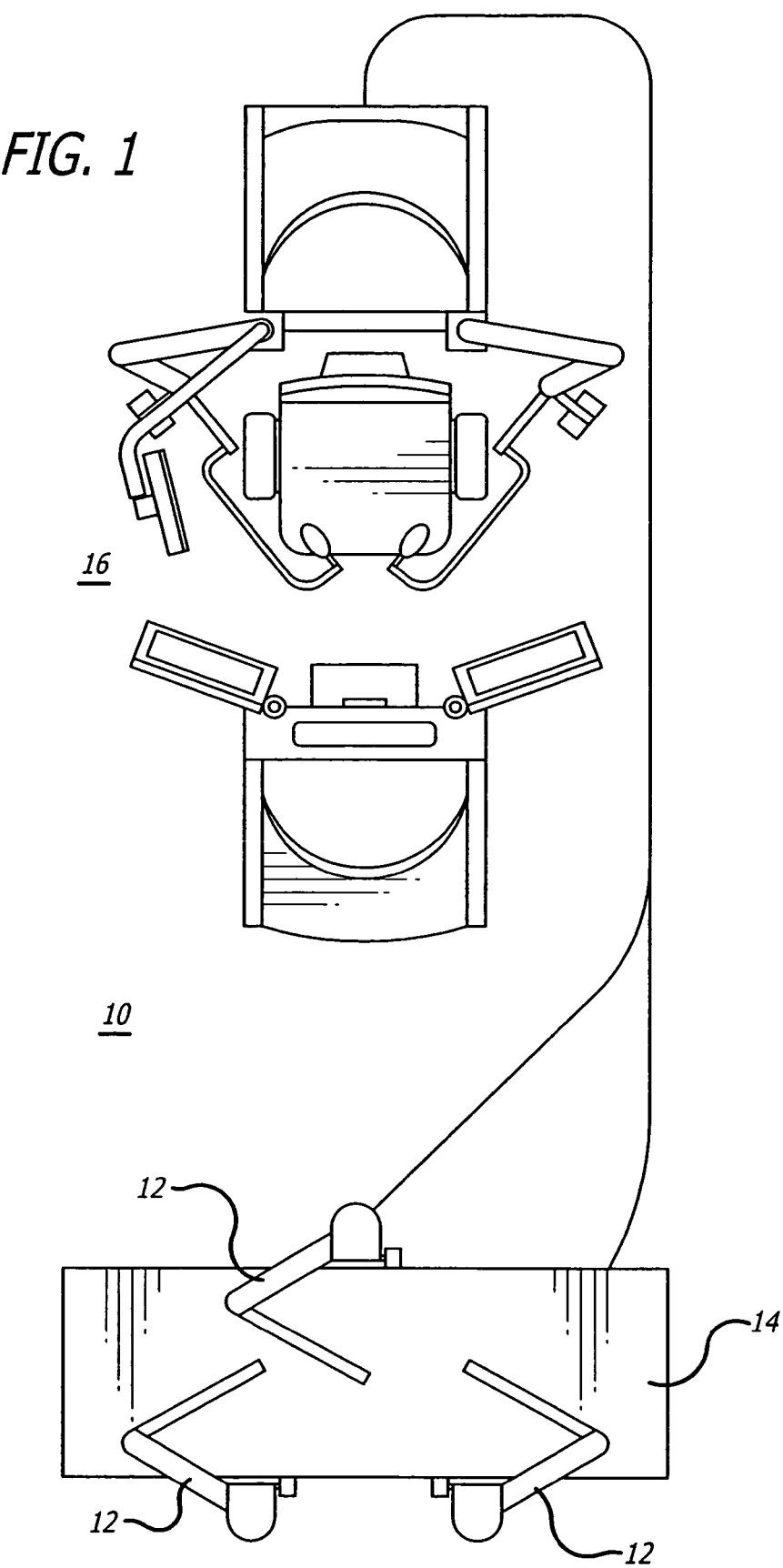
FIG. 1 is a top view of an illustration of a robotic system.

Referring to the drawings more particularly by reference numbers, FIG. 1 shows a robotic system 10. The system 10 may include a plurality of robotic arms 12 located adjacent to a table 14. Two of the robotic arms 12 may control the movement of corresponding medical instruments (not shown). The third robotic arm 12 may control the movement of an endoscope (not shown). The robotically controlled instruments and endoscope may be used to perform a minimally invasive medical procedure on a patient lying on the table 14.

The robotic arms 12 and accompanying instruments may be the same or similar to robotic products sold by Computer Motion under the trademarks AESOP and ZEUS. Although three robotic arms 12 are shown and described, it is to be understood that the system 10 may have a different number of arms 12.

The robotic arms 12 are controlled from a "surgeon" area 16. The surgeon area 16 may be located adjacent to the table 14. Alternatively, the surgeon area 16 may be coupled to the robotic arms 12 through a telecommunications link to allow a surgeon to have remote input into the system 10.

Figure 2:
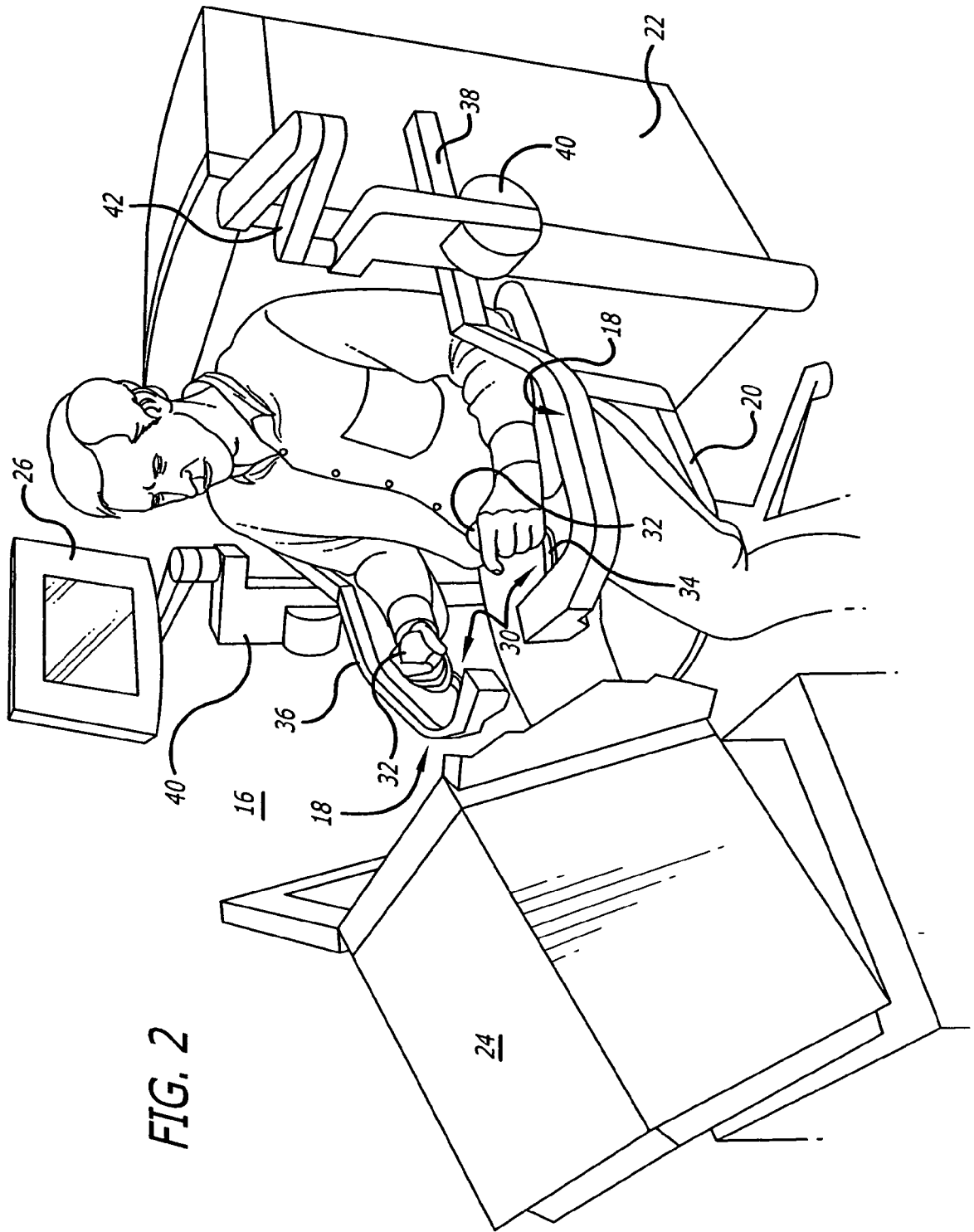
FIG. 2 is a perspective view of a surgeon control area of the robotic system.

FIG. 2 shows a surgeon area 16. The surgeon area 16 includes a pair of handle assemblies 18 located adjacent to a surgeon's chair 20. The handle assemblies 18 are coupled to a controller 22 that is also coupled to the robotic arms 12 and medical instruments. The controller 22 may include one or more microprocessors, memory devices, drivers, etc. that convert input information from the handle assemblies 18 into output control signals which move the robotic arms and/or actuate the medical instruments.

The surgeon's chair 20 and handle assemblies 18 may be in front of a video console 24. The video console 24 may be linked to the endoscope to provide video images of the patient. The surgeon's area 16 may also include a computer screen 26 coupled to the controller 22. The screen 26 may display graphical user interfaces (GUIs) that allow the surgeon to control various functions and parameters of the system 10.

Each handle assembly 18 may include a handle/wrist assembly 30. The handle/wrist assembly 30 has a handle 32 that is coupled to a wrist 34. The wrist 34 is connected to a forearm linkage 36 that slides along a slide bar 38. The slide bar 38 is pivotally connected to an elbow joint 40. The elbow joint 40 is pivotally connected to a shoulder joint 42 that is attached to the controller 22.

Figure 3:
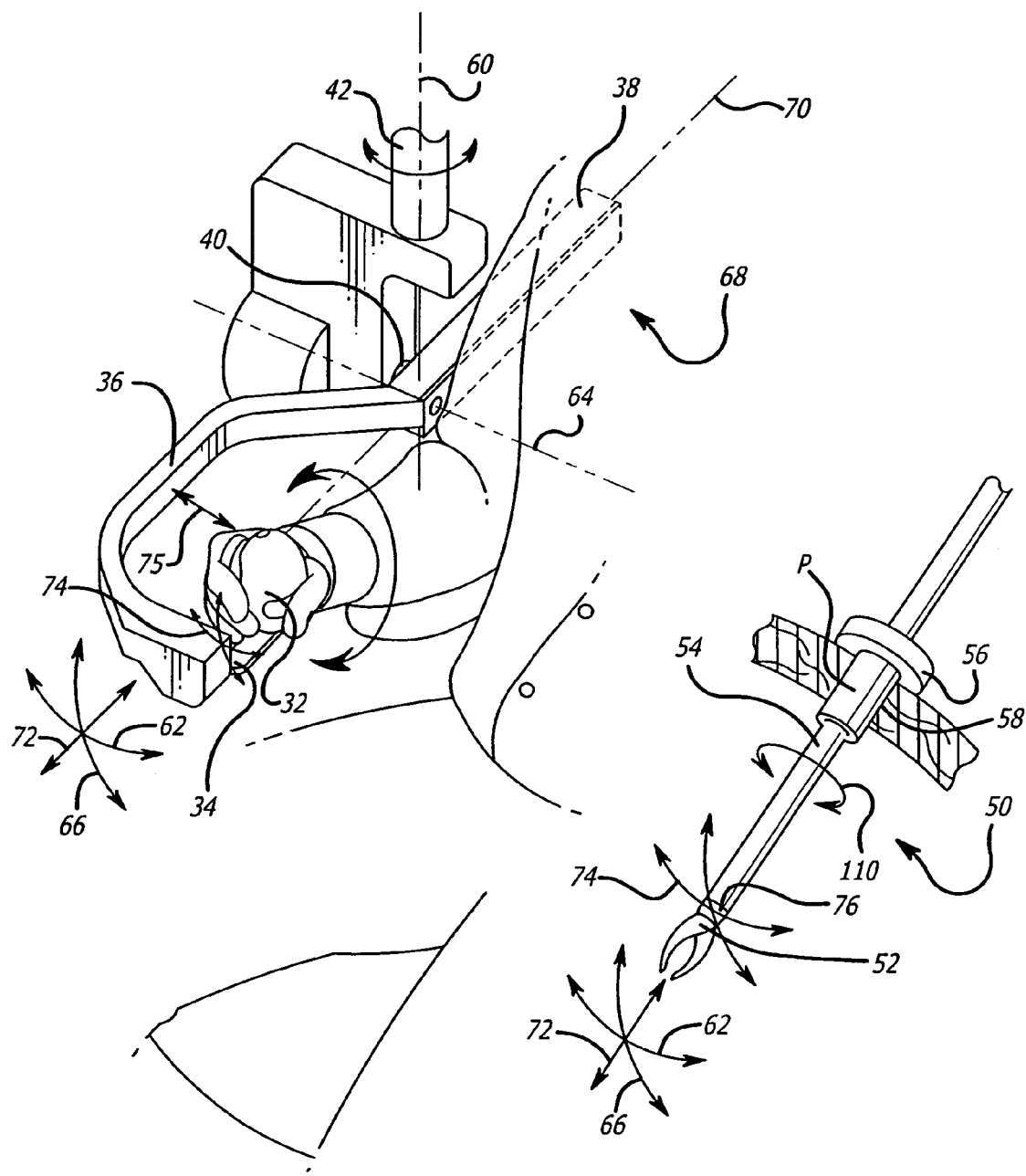
FIG. 3 is a perspective view of a handle assembly of the robotic system used to control a medical instrument.

FIG. 3 shows a handle assembly 18 superimposed with a medical instrument 50. The instrument 50 includes an end effector 52 attached to an instrument shaft 54. The shaft 54 extends through a cannula 56 inserted through an incision of a patient 58. The incision defines a pivot point P for the medical instrument 50.

The shoulder joint 42 includes a sensor (not shown) that provides feedback on the movement of the handle 32 about a shoulder axis 60. The sensor may be a mechanical encoder, optical encoder, etc. or other device which provides an output signal that corresponds to a position of the handle 32 about the shoulder axis 60. The output of the shoulder sensor is provided to the controller 22. The controller 22 performs a series of computations to determine a corresponding movement of the medical instrument 50. The computations may include one or more transformation and kinematic equations. The controller 22 provides output signals to the corresponding robotic arm 12 to move the instrument 50 about point P as indicated by the arrow 62.

The elbow joint 40 includes a sensor (not shown) that provides positional feedback on the position of the assembly about an elbow axis 64. The controller 22 utilizes the positional feedback to drive the robotic arm and move the instrument in the direction indicated by the arrow 66.

The forearm linkage 36 and slide bar 38 create a translator 68 that allows linear movement of the linkage 36 along a translator axis 70. The translator axis 70 intersects with the axes 60 and 64. The translator 68 has a sensor (not shown) that provides feedback information that is used to drive the robotic arm and move the instrument 50 in the direction indicated by the arrows 72.

When transforming movement of the handle 32 to movement of the instrument 50 the controller 22 may equate the intersection of the axes 60, 64 and 70 to the instrument pivot point P. Equating the intersection of the axis 60, 64 and 70 with the pivot point P provides a kinematic relationship such that the surgeons "feel" like they are actually moving the instrument 50. Additionally, the length of the forearm linkage and location of the handle are such that the surgeon is provided with the sensation that they are holding and moving the distal end of the instrument. These relationships also improve the ergonomics of the handle assembly and the ease of use of the robotic system as a whole. The transformation and kinematic equations may be similar to the equations used in the AESOP and ZEUS products.

The wrist 34 may have two degrees of freedom that cause corresponding movement, indicated by arrows 74, about a wrist 76 of the instrument 50. The wrist 34 may have sensors (not shown) that provide feedback information. The controller 22 can generate output signals to move the end effector 52 about the wrist 76 in a manner that corresponds to movement of the handle wrist 34. The handle 32 may have a degree of freedom for corresponding movement, indicated by arrow 75, for activating the end effector 52.

Figure 4:
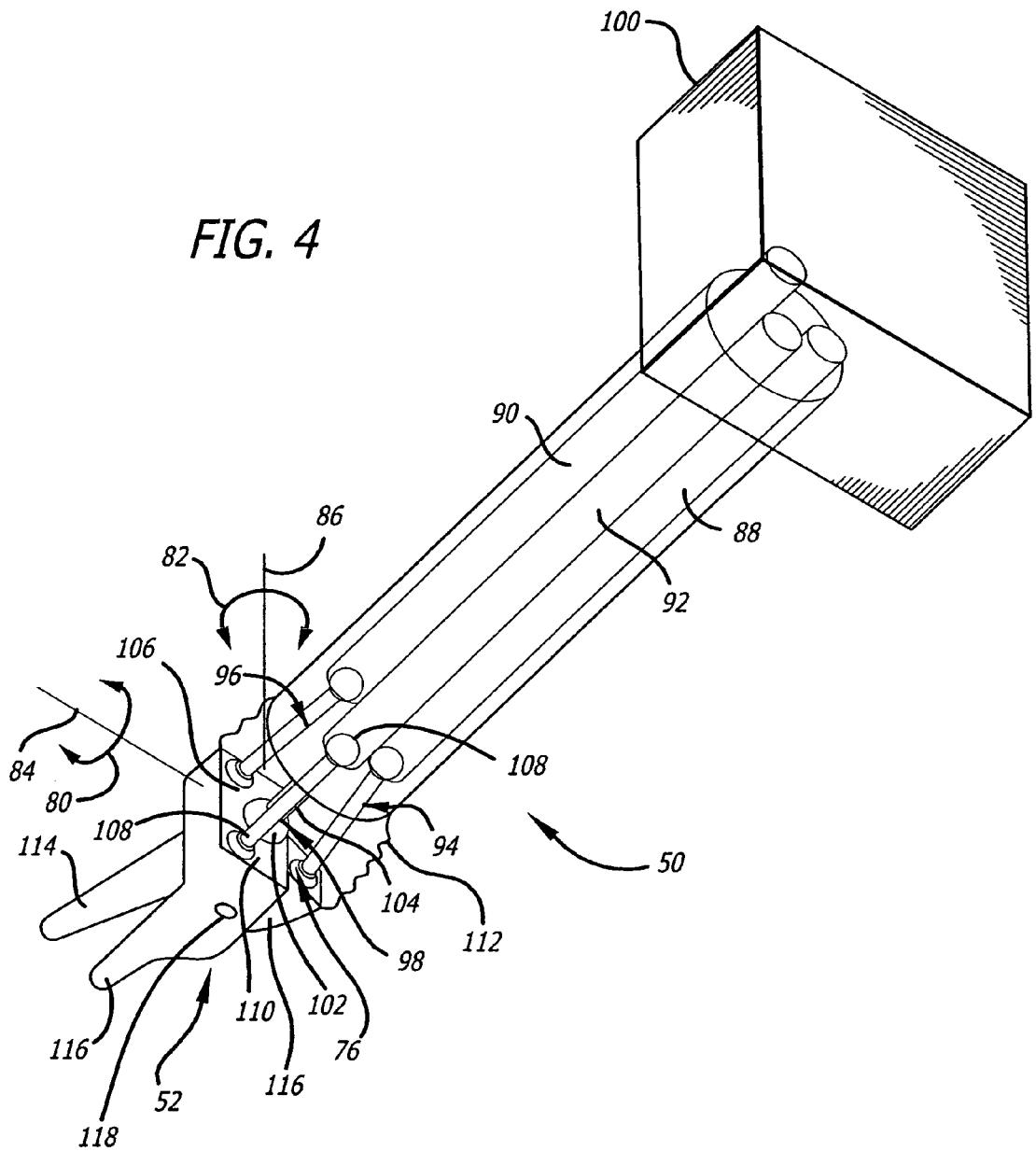
FIG. 4 is an enlarged perspective view of a medical instrument.

FIG. 4 shows an embodiment of a medical instrument 50. The instrument 50 includes an end effector 52 coupled to the wrist 76. The wrist 76 provides the end effector 52 with the two degrees of freedom indicated by arrows 80 and 82. These degrees of freedom correspond to arrows 74 shown in FIG. 3. The degrees of freedom extend about two axes 84 and 86 that intersect at a center pivot point of the wrist 76. Both degrees of freedom 80 and 82 provide pivot movement about the same pivot point.

The wrist 76 has linkages 94, 96 and 98 which may be coupled to a plurality of pins 88, 90 and 92, respectively, by ball joints 108. The pins 88, 90 and 92 may be coupled to a tool driver 100. The tool driver 100 may be a device that pushes and pulls the pins 88, 90 and 92. The tool driver 100 may include three driver motors similar to the single driver motor and interface shown and described in U.S. Pat. No. 6,007,550 issued to Wang et, al, and assigned to the same assignee, which is hereby incorporated by reference.

The wrist 76 may include a ball joint 102 that is attached to a stationary pin 104 and seated within a base 106 of the end effector 52. The instrument 50 may be constructed so that the pivot point is located at the center of the ball joint 102. Alternatively, the wrist 76 may include a universal joint that allows movement of the end effector 52 about the pivot point.

The linkages 94, 96 and 98 may also be coupled to the end effector 52 by ball joints 108. The ball joints 102 and 108 may be captured by an end plate 110 that is attached to the base 106 of the end effector 52. The wrist 76 may further have a bellows 112 to cover the linkages 94, 96, 98 and transmit torque from the end effector 52 to the shaft of the instrument 50.

Figure 5:
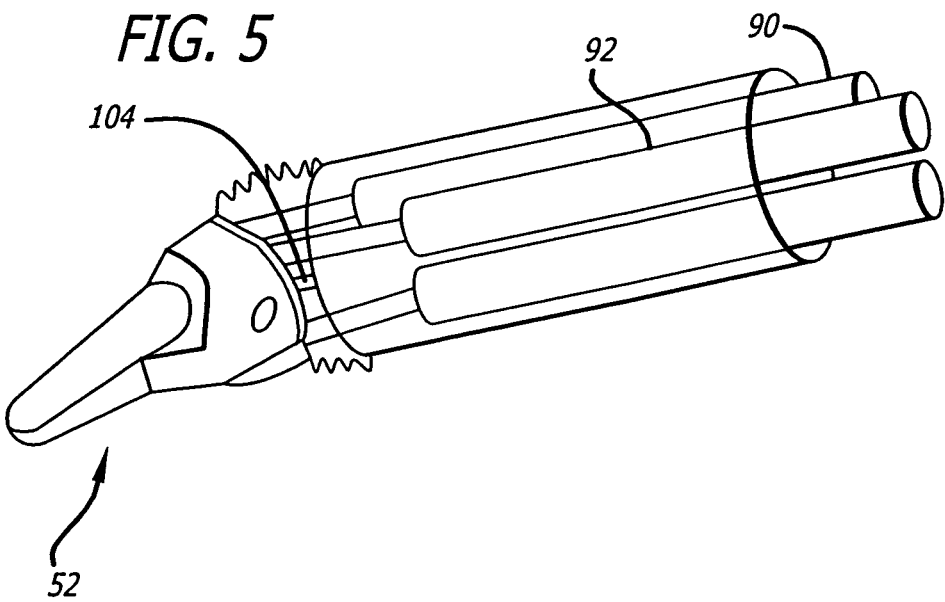
FIG. 5 is an enlarged perspective view of the medical instrument showing an end effector pivoted along a first degree of freedom.

As shown in FIG. 5, the end effector 52 can be moved along the first degree of freedom by pulling pin 92 and pushing pin 90. Likewise, the end effector 52 can be pivoted along the first degree of freedom by pushing pin 92 and pulling pin 90.

Figure 6:
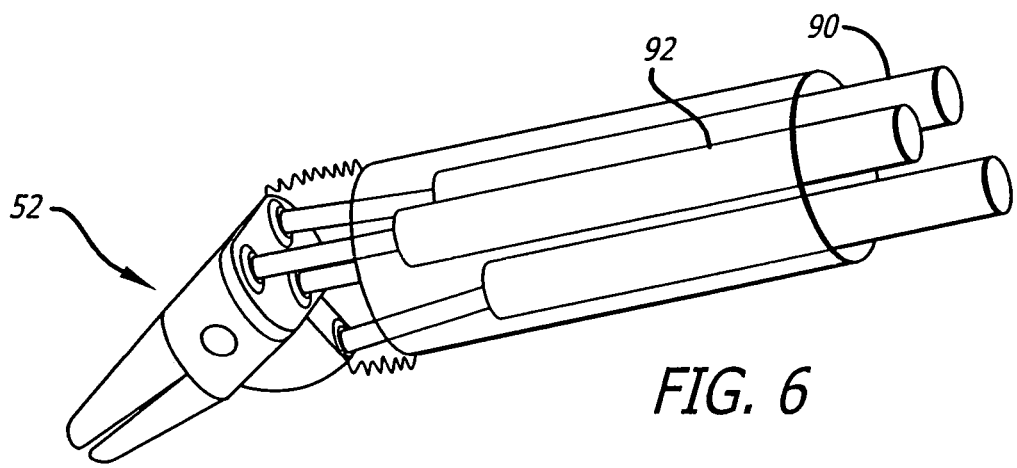
FIG. 6 is an enlarged perspective view of the medical instrument showing the end effector pivoted along a second degree of freedom.

As shown in FIG. 6, the end effector 52 can be moved in the second degree of freedom by pushing both pins 90 and 92. Likewise, the end effector 52 may be pivoted along the second degree of freedom by pulling both pins 90 and 92.

Figure 7:
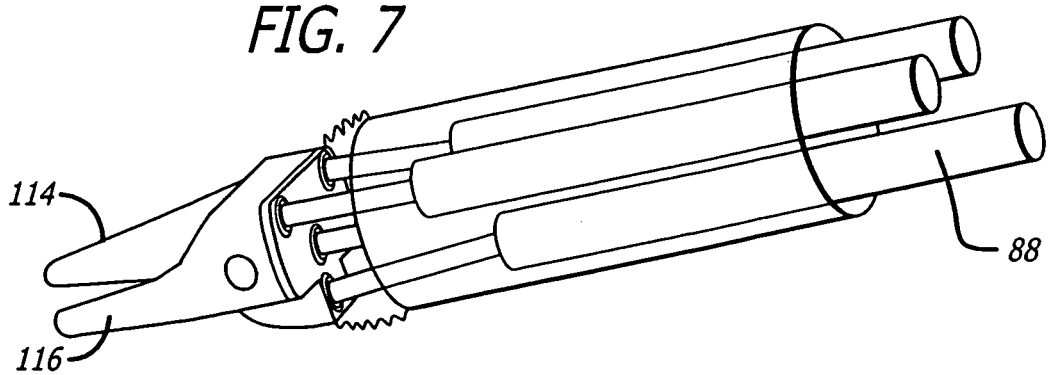
FIG. 7 is an enlarged perspective view of the medical instrument showing an actuated end effector.

As shown in FIG. 7, pin 88 can be pushed to move a movable jaw 114 of the end effector 52 away from a stationary jaw 116 to an open position. A pin 118 pivotally connects jaws 114 and 116. The moveable jaw 114 can be moved toward the stationary jaw 116 to a closed position by pulling the pin 88. Although a grasper is shown, it is to be understood that the end effector 52 may be of different types, such as a scissor or cauterizor.

The pins 88, 90 and 92 are pushed and pulled to move and actuate the end effector 52 in accordance with movement of the handle 32.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotically controlled medical instrument, comprising:
   an end effector having a base and a manipulatable element;
   a wrist mechanism having first and second linkages coupled to the base of the end effector;
   an elongate tube dimensionally insertable through a minimally invasive incision into a patient; and
   first, second, third, and fourth pins extending through the elongate tube, wherein the fourth pin is always stationary relative to at least the first and second pins and coupled by a ball joint to the base of the end effector at a pivot point, wherein the first and second pins are respectively coupled to the first and second linkages of the wrist mechanism to cause movement of the end effector in first and second degrees of freedom about the pivot point according to push/pull movement of the first and second pins, wherein movement of the first and second pins in a same push/pull direction results in the first degree of freedom movement of the end effector and movement of the first and second pins in different push/pull directions results in the second degree of freedom movement of the end effector, and wherein the third pin is coupled to the manipulatable element of the end effector to cause manipulation of the manipulatable element according to push/pull movement of the third pin.

2. The robotically controlled medical instrument according to claim 1, wherein the first and second degrees of freedom represent rotations about respective coordinate axes having the pivot point as origin.

3. The robotically controlled medical instrument according to claim 1, wherein the end effector further has a stationary jaw attached to the base and the manipulatable element comprises a moveable jaw pivotally coupled to the stationary jaw.

4. The robotically controlled medical instrument according to claim 3, wherein the stationary and moveable jaws are configured to form a grasper.

5. The robotically controlled medical instrument according to claim 3, wherein the stationary and moveable jaws are configured to form a scissors.

6. The robotically controlled medical instrument according to claim 1, wherein the first and second linkages are rotatably coupled at their distal ends to the base respectively by first and second ball joints.

7. The robotically controlled medical instrument according to claim 1, wherein the first and second linkages are rotatably coupled at their proximal ends to the first and second pins respectively by third and fourth ball joints.

8. The robotically controlled medical instrument according to claim 1, wherein the base is rectangular shaped, the first and second linkages are rotatably coupled at their distal ends to corners of the rectangular shaped base, and the pivot point is displaced from a line extending between the corners rotatably coupled to the distal ends of the first and second linkages.

9. The robotically controlled medical instrument according to claim 1, wherein the pivot point is located in an area bounded by a connection point of the third pin to the manipulatable element and connection points of the first and second linkages to the base.

10. The robotically controlled medical instrument according to claim 1, wherein the first pin, the second pin, and the third pin are disposed around the fourth pin.

11. A robotically controlled medical instrument, comprising:
an end effector having a base and a manipulatable element;
a wrist mechanism having first and second linkages coupled to the base of the end effector;
an elongate tube dimensionally insertable through a minimally invasive incision into a patient; and
first, second, third, and fourth pins extending through the elongate tube, wherein the fourth pin is always stationary relative to at least the first and second pins and coupled by a ball joint to the base of the end effector at a pivot point, wherein the first and second pins are respectively coupled to the first and second linkages of the wrist mechanism to cause movement of the end effector in first and second degrees of freedom about the pivot point according to push/pull movement of the first and second pins, wherein the first and second linkages are rotatably coupled at their distal ends to the base respectively by first and second ball joints, and wherein the third pin is coupled to the manipulatable element of the end effector to cause manipulation of the manipulatable element according to push/pull movement of the third pin.

12. The robotically controlled medical instrument according to claim 11, wherein the first and second degrees of freedom represent rotations about respective coordinate axes having the pivot point as origin.

13. The robotically controlled medical instrument according to claim 11, wherein the end effector further has a stationary jaw attached to the base and the manipulatable element comprises a moveable jaw pivotally coupled to the stationary jaw.

14. The robotically controlled medical instrument according to claim 11, wherein the first and second linkages are rotatably coupled at their proximal ends to the first and second pins respectively by third and fourth ball joints.

15. The robotically controlled medical instrument according to claim 11, wherein the base is rectangular shaped, the first and second linkages are rotatably coupled at their distal ends to corners of the rectangular shaped base, and the pivot point is displaced from a line extending between the corners rotatably coupled to the distal ends of the first and second linkages so that the movement of the first and second pins in a same push/pull direction results in the first degree of freedom movement of the end effector and movement of the first and second pins in different push/pull directions results in the second degree of freedom movement of the end effector.

16. The robotically controlled medical instrument according to claim 11, wherein the pivot point is located in an area bounded by a connection point of the third pin to the manipulatable element and connection points of the first and second linkages to the base.

17. The robotically controlled medical instrument according to claim 11, wherein the first pin, the second pin, and the third pin are disposed around the fourth pin.

18. A robotically controlled medical instrument, comprising:
an end effector having a base and a manipulatable element;
a wrist mechanism having first and second linkages coupled to the base of the end effector;
an elongate tube dimensionally insertable through a minimally invasive incision into a patient; and
first, second, third, and fourth pins extending through the elongate tube, wherein the fourth pin is always stationary relative to at least the first and second pins and coupled by a ball joint to the base of the end effector at a pivot point, wherein the first and second pins are respectively coupled to the first and second linkages of the wrist mechanism to cause movement of the end effector in first and second degrees of freedom about the pivot point according to push/pull movement of the first and second pins, wherein the pivot point is located in an area bounded by a connection point of the third pin to the manipulatable element and connection points of the first and second linkages to the base, and wherein the third pin is coupled to the manipulatable element of the end effector to cause manipulation of the manipulatable element according to push/pull movement of the third pin.

19. The robotically controlled medical instrument according to claim 18, wherein the first and second degrees of freedom represent rotations about respective coordinate axes having the pivot point as origin.

* * * * *